United States Patent [19]

Demoment et al.

[11] Patent Number: 5,229,716
[45] Date of Patent: Jul. 20, 1993

[54] PROCESS AND DEVICE FOR REAL-TIME SPECTRAL ANALYSIS OF COMPLEX UNSTEADY SIGNALS

[75] Inventors: Guy Demoment, Orsay; Alain Herment, Paris; Claude Arcile, Igny; Indira Mouttapa, Paris, all of France; Amrane Houacine, Bab Essouar, Algeria; Pierre Peronneau, Paris, France

[73] Assignee: Institut National de la Sante et de la Recherche Medicale, France

[21] Appl. No.: 776,400

[22] PCT Filed: Mar. 22, 1990

[86] PCT No.: PCT/FR90/00193

§ 371 Date: Nov. 21, 1991

§ 102(e) Date: Nov. 21, 1991

[87] PCT Pub. No.: WO90/11494

PCT Pub. Date: Oct. 4, 1990

[30] Foreign Application Priority Data

Mar. 22, 1989 [FR] France ................................ 8903761

[51] Int. Cl.[5] ............................................. G01R 33/20
[52] U.S. Cl. ...................................... 324/307; 324/306
[58] Field of Search ........... 364/422; 324/77 R, 77 A, 324/78 R, 306, 300, 309, 307, 308, 310, 311, 312, 313, 314, 318, 322; 128/653.5

[56] References Cited

U.S. PATENT DOCUMENTS

| 4,391,149 | 5/1981 | Herzl ................................ 73/861.25 |
| 4,585,992 | 4/1986 | Maudsley et al. .................. 324/309 |
| 4,789,832 | 12/1988 | Nagayama ........................ 324/312 |
| 5,019,978 | 5/1991 | Howard, Jr. et al. ............. 364/422 |

FOREIGN PATENT DOCUMENTS 63-042209 8/1991 Japan .

OTHER PUBLICATIONS

Ultrasonics, vol. 24, No. 4, Jul. 1986, Butterworth & Co., Ltd., (Guilford, GB)-R. P. Williams: "On the relationship between velocity distribution and power spectrum of scattered radiation in doppler ultrasound measurements on moving suspensions", pp. 197-200.

Journal of Magnetic Resonance, vol. 61, 1985, Academic Press Inc., H. Barkhuijsen et al.: "Retrieval of frequencies, amplitudes, damping factors, and phases from time-domain signals using a linear least-squares procedure", pp. 465-481.

Primary Examiner—Michael J. Tokar
Attorney, Agent, or Firm—Larson and Taylor

[57] ABSTRACT

The invention includes a real time spectral analysis of unsteady signals with complex values representatives of a physical phenomenon. Successive sections of a sample signal are modelled by a high order self-regressive process by estimating parameters characterizing the model by rapid Kalman filtering using an algorithm.

6 Claims, 2 Drawing Sheets

PROCESS AND DEVICE FOR REAL-TIME SPECTRAL ANALYSIS OF COMPLEX UNSTEADY SIGNALS

The invention relates to the real-time adaptive spectral analysis of unstable signals having complex values representing a physical phenomenon.

The invention can be used whenever it is necessary to analyse in real time such signals which can be represented by a self-regressing parametric model, by assuming that the coefficients of the model remain steady over short time intervals. It applies more particularly to all the fields of medical imagery, for example using NMR, and more generally whenever spectral analysis must be made on organic signals, for example in electrocardiography and electro encephalography. It finds however a particularly important application in the spectral analysis of the signals furnished by ultrasonic Doppler velocimeters for studying the blood flow in the heart cavities or the vessels.

At the present time, parametric spectral analysis is relatively little used in Doppler velocimetry and in medical ultrasonic echography. It remains at the laboratory stage. It consists in modelling the signals using a parametric model, generally of the adjusted mean self-regressing type, whose parameters are adjusted by optimization using algorithms of the least square type. This approach has the advantage of working on short signal sections but it involves using low order models and has consequently limited frequency resolution, which is particularly troublesome for the spectral analysis of very unsteady signals. Moreover, the known methods do not process the demodulated signals with complex values as such, but process each of the components separately, respectively in phase and in quadrature.

Commercial apparatuses use non parametric spectral analysis methods of Fourier analysis type so as to be able to use them with rapid Fourier transformation algorithms. But these methods require working on long sections of the signals so as to obtain a suitable estimate of the desired spectral representation, which is incompatible with the nature of the unsteady states met with in the above mentioned fields.

The invention aims more particularly at providing a spectral analysis process and device answering better than those known heretofore the requirements of practice, particularly in that they improve the frequency resolution, make possible a more accurate analysis of the signals and restrict the variability of the spectra obtained for representing flows in closely related conditions.

To this end, the invention proposes more particularly an adaptive spectral analysis process by modelling the phenomenon represented by the signal characterized in that successive sections of the sampled signal are modelled, using a high order self-regressing process, close or equal to the maximum authorized by the duration of the sections and the sampling frequency, by making an estimate of the parameter characterizing the model by rapid Kalman filtering using an algorithm which is simplified in the full limit authorized by the local steady state of the model in the section and in that the spectral power density is determined from the estimated parameters; to avoid risks of instability related to the choice of the high order, the estimate of the parameters of the self-regressing model are regularized by using a constraint which consists in minimizing a criterion of the form $$J_2(a) = J^1(a) + \Omega(a)$$

where $J_1$ (a) is the sum of the least squares $[y(n) - z(n)]^2$, z designating the sampled function modelling the signal via the parameters a to be determined and y the function represented by the samples of the signal and where $\Omega(a)$ is a regularizing function taking into account the a priori knowledge of the nature of the function or obtained by optimization.

Through using a high order model, very good frequency definition is obtained. The process makes it possible to obtain parameters directly for calculating the spectral power density of the signal in the analysis window. It is in particular possible to use a model order equal to the number of sampling points in the Doppler signal, which gives an excellent frequency definition, whereas the present-day spectral analysis methods using a self-regressing model and criterion of the least squares have an order of size three to seven times less than the number of sampled points.

The invention also provides a spectral analysis device which can be directly fitted to a conventional Doppler velocimeter, without modifying the existing probe and its associated electronic circuits, nor its display means.

The invention will be better understood from the following description of the process and device according to the invention and the reasoning which led to it. It refers to the accompanying drawings in which.

MODELLING THE UNSTEADY SIGNALS

Before starting the description of the invention, information will be recalled concerning the modelling of the signals representing unsteady phenomena and concerning the regularization of the model.

In the case where the unsteady state of the signal is sufficiently slow with respect to the speed of variation of the amplitude of the signal, the latter may be considered as "locally steady", i.e. steady over an analysis section of N samples, N being typically a few tens or so. The samples observed y(n), n = 1,2,...,N are described by a self-regressing model (AR) expressed by:

$$y(n) = z(n) + b(n) \qquad (1)$$

$$z(n) = \sum_{i=1}^{p} a_i y(n-i) = a^t y_p(n) \qquad (2)$$

with $$\begin{cases} a^t = a_p, a_{p-1}, \ldots, a_1] \\ y_p(n)^t = y(n-p), \ldots, y(n-1)] \end{cases} \qquad (3)$$

where $a^t$ is the vector of the coefficients of the model whose order is p and where b(n) represents the procedure generating the signal, of unknown variance $\sigma^2$.

The spectral analysis is then made following a criterion which is often that of the least squares, which consists in minimizing $J_1(a)$:

$$J_1(a) = \sum_{n=1}^{N} [y(n) - z(n)]^2 \quad (4)$$

Since the model is linear, the calculating algorithms are rapid. But obtaining a good approximation is subordinated to the choice of an order p as high as possible; now, if we take p close to N or equal thereto, the minimization of $J_1$ is not a satisfactory criterion because of the excessive variance of the solution.

To overcome this difficulty and stabilize the solution, it has been proposed to regularize the model by adding a stabilizing function to $J_1$, which makes it possible to keep a high value of p (close to or even equal to N). The criterion then consists in minimizing $J_2(a)$:

$$J_2(a) = J_1(a) + \Omega(a) \quad (5)$$

where (a) is a regularizing function, numerous examples of which exist.

This function will however as a general rule be of the form:

$$\Omega(a) = |a - a_0|^t M(a - a_0)$$

$\Omega$ is therefore scalar, product of the transposed matrix $|a - a_0|^t$, of a positive symmetrical and defined matrix of dimension p.p (p being the dimension of a) and $(a - a_0)$. The transpose is obviously a line vector.

If M is the identity matrix, we arrive at the simplified form which will be given at (7) further on.

The choice of the regularizing function $\Omega$ (a) translates the a priori information about the nature of the local spectral properties of the analyzed signal. This information is that the unknown spectral power density is a "smooth" function, i.e. having a certain regularity, compared with an unorganized spectrum formed of a multitude of spectral rays without any relation with each other. For reasons of convenience of implementation, a quadratic function is chosen, which has the advantage of leading to an explicit and linear solution with respect to the values observed y(n).

A measure of "spectral smoothness" is formed by $$D_k = \int_{-1/2}^{1/2} \left| \frac{\partial^k H(f)}{\partial f^k} \right|^2 df$$

$$k = 0, 1, 2, \ldots$$

where H(f) is the frequency transfer function of the bleaching filter for the analyzed signal, which is also the inverse of its generating filter which is described by the equations (1) and (2). A high value of $D_k$ signifies a non smooth spectral power density, all the more so the higher the order k of the drift. A zero order spectral smoothness is used:

$$D_o = \int_{-1/2}^{1/2} |H(f)|^2 df : 1 + \sum_{m=1}^{P} a_m^2$$

which is, except for a constant, the euclidean norm of the vector of the parameters a, which leads in most cases to adopting the regularizing functional:

$$\Omega(a) = \mu \sum_{m=1}^{P} a_m^2 \; \mu \epsilon \; IR^+ \quad (6)$$

where the coefficient $\mu$ is a positive real number called "regularizing coefficient" and which, as will be seen, plays a very great role in the operation of the invention and which is chosen by an a posteriori likelihood maximum method.

REGULARIZATION MODELLING ACCORDING TO THE INVENTION

The invention uses a procedure which may be considered as in two steps, based particularly on the fact that, in practice, the signals are very often signals for which a local study of the phenomenon may be made by dividing the time horizon into blocks of length N and that an assumption may be made of a local steady state in each block, so as to be able to use the properties of local invariance of the model by then carrying out an adaptive spectral analysis reflecting a slow variation of the parameters with respect to the amplitude fluctuations of the signal, namely:

1. A locally steady model is sought, i.e. an equivalent invariant model defined by the optimum of the criterion (5) calculated over a reduced time window, by making a compromise between too great a window length (which does not allow the unsteady states of the signal to be followed faithfully) and too short a length (which does not allow the model to be estimated under good conditions), which leads to choosing an AR model of the highest order p possible, close to N or equal to N, which involves stabilizing the model.

This model is sought for the value of the regularization coefficient and that of the variance $\sigma^2$ of the generator process which make the likelihood of the model maximum.

2. The calculations for maximizing the likelihood of the model are simplified by adopting a sub-optimum solution:
the variation range of $\mu$ of the equation (6) of the minimization criterion is reduced to a finite preselected set of discrete values, and
using an algorithm which may be rapid, the optimum solution â and possibly the corresponding likelihood $V(\sigma^2, \mu/y)$ are calculated from samples of the observed signal, so as to select the highest.

The first step leads to organizing the samples of the signal in consecutive blocks of length N and carrying out regularization on each block. A constraint is imposed relating the set of parameters locally and translating spectral smoothness information: that leads to minimizing, on each of the blocks, a criterion of the form:

$$J_2(a) = J_1(a) + \mu |a - a_0|^2 \quad (7)$$

When the process generating the analyzed signal is assumed Gaussian, that is tantamount to admitting that the parameters a are characterized, in a Bayesian interpretation, by the law of a priori probability:

$$f(a/a_0, \mu, \sigma^2) \propto \exp\left(-\frac{\mu}{2\sigma^2}|a-a_0|^2\right)$$

The vector of the AR parameters is initialized by choosing $a_{O=0}$ in the case of a steady signal. It will be seen further on that this manner of proceeding may be kept for certain unsteady signals. In the other cases, for each current block, the result of calculating the preceding block will be chosen when the blocks are adjacent.

It still remains to fix the value of $\mu$ and $\sigma^2$ for minimizing the criterion (7). This choice is made, as was mentioned above, by maximizing the likelihood of the model. It will be seen that $\mu$ and $\sigma^2$, called hyperparameters, may be decoupled in this maximization.

To explain the first step, the equations of state associated with the problem should be given and it should be shown how the standard Kalman filter (which is based on a Riccati equation not using the local steady state of the model which is at the basis of the adaptive methods, nor the property of shift of the successive vectors $y_p(n)$ which is the consequence of the choice of an AR model) a simpler filter may be substituted, using Chandrasekhar's equations for calculating the parameters a which minimize, with $\mu$ and $\sigma^2$ fixed, the criterion (7), as well as for calculating the corresponding likelihood. It will be seen that this filter, with invariant state model, allows the regularization constraint to be introduced.

For that, these properties are caused to appear explicitly by defining an "extended vector-parameter" or state vector with m components:

$$a_m(i) = [0^t{i-1}, {}^ap, {}^ap-1, \ldots, a_1 1, 0, 0, \ldots, 0]^t, \text{ with } m > p$$

and the overall vector of the data is considered:

$$y_m = y(p+1), y(-p+2), \ldots, y(0), y(1), \ldots, y(m-p)^t.$$

The linear model defined by the equations (1) and (2) may then be in the form of the following equivalent state model:

$$a_m(i+1) = D a_m(i) \quad i = 1, 2, \ldots$$

$$y(i) = y^t_m a_m(i) + b(i)$$

where D is the shift operator:

$$D = \begin{bmatrix} 0 & 0 & & & & \\ 1 & 0 & 0 & & & \\ 0 & 1 & 0 & & & \\ \cdot & \cdot & \cdot & & & \\ 0 & \cdot & 0 & 1 & 0 \end{bmatrix}$$

The calculation of the solution may then be effected by the following Kalman filter:

$$\hat{a}_m(i+1/i) = D\hat{a}_m(i/i-1) + k_m(i)r(i)^{-1}y(i) - y^t_m \hat{a}_m(i/i-1) \quad (8)$$

$$\begin{aligned} r(i) &= y_m{}^t P_m(i/i-1)\bar{y}_m + 2 \\ k_m(i) &= D P_m(i/i-1)\bar{y}_m \\ P_m(i+1/i) &= D P_m(i/i-1)D^t - k_m(i)r(i)^{-1}k_m{}^*(i) \end{aligned} \quad (9)$$

with the initial conditions:

$$\begin{aligned} a_m(1/0) &: [a(1/0), 0, \ldots, 0]^t \\ r(1) &= y_m{}^t(1/0)y_m + \sigma^2 \\ K_M(1) &= D P_m(1/0)y_m \\ P_m(1/0) &= \frac{P(1/0) \mid 0}{0 \mid 0} \quad P(1/0) = \tau^2 I = \frac{\sigma^2}{\mu} I \end{aligned} \quad (10)$$

where $\bar{y}_m$ designates the simply conjugated vector of vector $y_m$ and $k^*$ designates the conjugate transposed matrix of k.

The introduction of such additional variables is apparently unfavourable, for it increases the dimensions of the state vector. But this impression is misleading for such introduction causes the invariance properties to appear explicitly, which are used.

It may moreover be verified that, at each recurrence, the number of non zero coordinates of the gain vector $k_m(i)$ remains equal to p.

Since this state model is invariant (D and $y_m$ being constant) and with steady variance ($\sigma^2$ being constant over a block), a rapid algorithm is obtained directly by replacing the standard equations by Chandrasekhar's equations. Not only do these equations allow rapid resolution, but they further make it possible to pass naturally to square root algorithms offering good digital stability.

Hereafter, by "algorithm B-CAR" will be designated the regularization rules using the algorithm, applied to blocks of a size appropriate to the nature of the signal. These equations only propagate the increments of the nominal quantities of the equation (9), which are themselves factorized. The direct application of such factorization techniques to the filter (8) (9) leads to the following equations:

$$\begin{aligned} v_m(i)^t &= y_m{}^t B(i) \\ w_m(i)^t &= v_m(i)^t M(i) \\ M(i+1) &= M(i) + w_m(i)r(i)^{-1}w_m(i)^t \\ k_m(i+1) &= k_m(i) + D B(i)w_m(i) \\ r(i+1) &= r(i) + v_m(i)^t w_m(i) \\ B(i+1) &= D B(i) - k_m(i+1)r(i+1)^{-1}v_m(i)^t \end{aligned} \quad (11)$$

In these equations, the fact is used that M and $P_m$ are matrices with Hermitian symmetry: $M^* = M$ and $P^*_m = P_m$. Condensed writing of the algorithm is obtained by projection, by only causing the components to appear which effectively come into play at each recurrence in the calculation. For that, an effective gain-vector k(i) is defined, of dimension p, containing the non zero coordinates of $k_m(i)$:

$$k_m(i) = [0^t{}_{i+1}, k(i)^t, 0^t{}_{m-p-i-1}]^t$$

Similarly, if $\alpha$ is the dimension of M(i), we may also write:

$$B(i) = [0_{\alpha,k}, S(i)^t, 0_{\alpha,m-p-i-1}]^t$$

where S(i) is a matrix of dimensions $[(p+1),\alpha]$. The algorithm may then be in the form:

$$\left. \begin{array}{l} v(i)^t = [y(i-p), y_p(i+1)^t]S(i) \\ w(i)^t = v(i)^t M(i) \\ M(i+1) = M(i) + w(i)r(i)^{-1}w(i)^t \\ r(i+1) = r(i) + v(i)^t w(i) \\ \left( \dfrac{0}{k(i+1)} \right) = \left( \dfrac{k(i)}{0} \right) + S(i)w(i) \\ S(i+1) = S(i) - \left[ \dfrac{0}{k(i+1)} \right] r(i+1)^{-1} v(i)^t \end{array} \right\} \quad (12)$$

the updating of the parameters taking place in accordance with:

$$a((i+1/i) + a(i/i-1) + k(i)r(i)^{-1}[y(i) - y_p(i)^t a(e/e-1)] \quad (13)$$

This algorithm has the advantage of applying not only to "pre-windowed" problems (processing of the steady case of an isolated block in the unsteady case) but also to covariance type problems (processing of adjacent blocks in the unsteady case).

Initialization of the algorithm is conditioned by the a priori covariance matrix P (1/0) from which B(1) and M(1) are derived, at the time of factorization of the initial increment:

$$\delta P_m(2) = P_M(2:1) - P_m(1/0) = B(1)M(1)B(1)^t$$

The initial covariance increment may also be written, returning to the equations, in extended form:

$$\delta P_m(2) = DP_m(1/0) D^t - k_m(1)r(1)^{-1}k_m(1)^* - P_m(1/0)$$

with $$P_m(1/0) = \left[ \begin{array}{c|c} P(1/0) & 0 \\ \hline 0 & 0 \end{array} \right]$$

In the general case, if we assume $$P(1/0) = v_0 \begin{bmatrix} 1 & v_1 & v_2 & \cdots \\ v^*_1 & 1 & v_1 & \cdots \\ \cdot & & & \\ \cdot & & & \\ v^*_{p-1} & \cdot & \cdot & \cdots \end{bmatrix}$$

then we may resolve $$DP_m(1/0) D^t - P_m(1/0) = v_0(s_m s^*_m + s_m g^*_m + g_m s^*_m) + v_0(v_m v^*_m + v_m d^*_m + d_m v^*_m)$$

where $$s^*_m = [1, 0, 0, \ldots]$$

$$g^*_m = [0, v_1, v_2, \ldots, v_{p-1}, 0, 0, \ldots]$$

$$v^*_m = [0, 0, \ldots, 0, 1, 0, 0, \ldots]$$

$$d^*_m = [0, v_{p-1}, v_{p-2}, \ldots, v_1, 0, 0, \ldots]$$

The matrix P(1/0) is chosen diagonal and the rank of $\delta_m P(2)$ is generally $\delta = 3$. Since the initial factorization is not unique, the signature matrix of $P_m(2)$ is advantageously chosen for M(1), which gives the beginning of a square root algorithm whose numerical qualities are better.

If the a priori covariance matrix P(1/0) is diagonal, the vectors gm and dm are identically zero and the initial increment $P_m(2)$ is reduced to:

$$\delta P_m(2) = -v_0 s_m s^*_m + v_0 v_m v^*_m - k_m(1)r(1)^{-1}k_m(1)^*,$$

of a rank at most equal to 3 since it is broken down into a sum of three dyadic or antiscalar matrices, each of a rank equal to 1. $\delta P_m(2)$ may also be written in the form:

$$\delta P_m(2) = B(1)M(1)B(1)^*$$

with, as central factor=

$$M(1) = \begin{bmatrix} -1 & 0 & 0 \\ 0 & -1 & 0 \\ 0 & 0 & 1 \end{bmatrix}$$

which leads, once the projection has been made so as obtain the reduced dimension algorithm, to:

$$S(1) = [k(1), b, c]$$

$$k(1) = [0, k(1)^t r(1)^{-\frac{1}{2}}]^t$$

$$k(1) = \frac{\sigma^2}{\mu} y_p(1)$$

$$b = [\tau, 0, 0, \ldots, 0]^t$$

$$c = [0, 0, 0, \ldots, \tau]^t$$

$$r(1) = y_m^t P_m(1/0) y_m + \sigma^2 = \frac{\sigma^2}{\mu} y_p(1)^t y_p(1) + \sigma^2$$

under the conditions, which are generally fulfilled, that:
the coefficients $a_i$ of the model, which are complex, have real and imaginary parts whose a priori laws of probability are normal, centred, independent and of variance $(\frac{1}{2})\tau^2$ (we thus find again the a priori covariance matrix $P(1/0) = \tau^2 I$),
the generator noise of the observed signal b(n), which is also complex, has real and imaginary parts whose a priori laws of probability are also normal, centred, independent and of variance $(\frac{1}{2})\sigma^2$.

This rigorous solution uses the values effectively observed prior to the initial time of the window in the general vector $y_m$. This method, which may be termed "covariance", assumes operating:
either on an isolated data block of a length twice the chosen order p,
or on a data block adjacent a prior block whose contents have been kept.

The down-count of the elementary arithmetic operations, limited to multiplications alone, shows that the complexity of this algorithm is $\theta(11p)$ by recurrence. If we choose p=N, it can be seen that the total complexity of processing N data is $\theta(N^2)$, which is normal for an algorithm of this type.

A solution for simplifying the algorithm may be termed "pre-windowing". It assumes that the p values prior to the initial time in the measurement window are zero, with for consequences:

$$k_m(1) = D\ P_m(1/0) y_m = 0$$

$$r(1) = \frac{\sigma^2}{\mu} y_p(1)^t y_p(1) + \sigma^2 = \sigma^2$$

$$\delta P_m(2) = v_0 s_m s^*_m + v_0 v_m v^*_m$$

The rank of the initial increment is $\alpha=2$. As initial factor we may choose:

$$M(1) = \begin{bmatrix} -1 & 0 \\ 0 & 1 \end{bmatrix}$$

$$S(1) = [b, c]$$

The complexity of the calculation is substantially reduced.

When the nature of the phenomenon represented by the signal is well known, the hyperparameters may be chosen a priori. In the opposite case, calculation of the likelihood of the hyperparameters is useful.

With a Kalman filter, the likelihood of the hyperparameters (or its logarithm) may be calculated by recurrence, using quantities intervening in the algorithm.

The search for the likelihood maximum amounts in fact to a problem of regularized least squares already represented by the equation (7). This problem has a simple Bayesian interpretation since the minimization of (7) is equivalent to maximizing the likelihood criterion V(a):

$$V(a) = \exp\left\{ -\frac{1}{2\sigma^2}\left( \sum_{n=1}^{N} [y(n) - z(n)]^2 + \mu \sum_{m=1}^{p} a_m^2 \right) \right\} \quad (15)$$

When the hyperparameters $\mu$, $\sigma^2$ are used, the calculation shows that the solution $\hat{a}$ is in fact the mean of the a posteriori law defined by the conditional distribution of the data:

$$f(y/a, \sigma^2) \propto \exp\left\{ -\frac{1}{2\sigma^2}\left( \sum_{n=1}^{N} [y(n) - z(n)]^2 \right) \right\}$$

and the a priori law:

$$f(a/\mu, \sigma^2) \propto \exp -\frac{\mu}{2\sigma^2} a^t a$$

We may then consider that this a priori law specifies a class of estimators via the parameters $\mu$ and $\sigma^2$. These are the hyperparameters of the problem. Since the laws are normal, the likelihood of the hyperparameters is represented by an integral:

$$V(\sigma^2, \mu, y) = \int f(y/a, \sigma^2) f(a/\mu, \sigma^2) da \quad (16)$$

The model to be chosen is that which maximizes this likelihood with respect to the hyperparameters. In this sense, the method is adaptive since the choice of a priori values may depend on the data.

Finally, by sequential application of Bayes rule to the relation, we obtain:

$$V(\mu, \sigma^2/y) = f[y(1)] \prod_{n=2}^{N} f[y(n)/y(1), \ldots, y(n-1)]$$

The conditional marginal density of y(n) is used which is possible to obtain from the observed samples $y(1), y(2), \ldots, y(n-1)$:

$$f[y(n)/y(1), \ldots, y(n-1)] =$$

$$\int f[y(n)/a] f[a/y(1), \ldots, y(n-1)] da =$$

$$\frac{1}{\sqrt{2\pi\sigma^2}} \exp\left\{ -\frac{1}{2\sigma^2}\left[ y(n) - \sum_{i=1}^{p} a(i) y(n-i) \right]^2 \right\}$$

The calculation of this conditional density requires knowing $\sigma^2$ and a. But, $$y(n) = y_p(n)^t a(n/n-1) + e(n)$$

where $\hat{a}(n/n-1)$ is the optimum estimate (i.e. conditional to the past $(y(1), y(2),\ldots,y(n-1))$, and where $e(n)$ is the innovation of the observed process. We also then have:

$$f[y(n)/y(1), \ldots, y(n-1)] = \frac{1}{\sqrt{2\pi\sigma_e(n)^2}} \exp\left( -\frac{e(n)^2}{2\sigma_e(n)^2} \right)$$

The variance of the innovation $\sigma_e(n)^2$ remains to be evaluated. But a Kalman filter is only sensitive to the relative variance alone of the observation noise (i.e. here of the generator process) and of the state noise (i.e. here of the a priori variance of the parameters). Since the recurrent calculation of $\hat{a}(n/n-1)$ only therefore depends on $\mu$ and not on the value of $\sigma^2$, we may take arbitrarily $\sigma^2=1$ in the algorithm: we then have:

$$\sigma_e(n)^2 r(n) = \sigma^2 [y^t_m P_m(n/n-1) y_m + 1]$$

whence we derive:

$$f[y(n)/y(1), \ldots, y(n-1)] = \frac{1}{\sqrt{2\pi\sigma^2 r(n)}} \exp\left( -\frac{e(n)^2}{2\sigma^2 r(n)} \right)$$

This formula shows that the two hyperparameters are decoupled. The estimate $\hat{\sigma}^2$ of $\sigma^2$ according to the likelihood maximum (marginal) is then:

$$\hat{\sigma}^2 = \frac{1}{N} \sum_{i=1}^{N} \frac{e(i)^2}{r(i)}$$

and the (marginal likelihood of $\mu$ is then:

$$L(\mu/y) = \frac{1}{2} \sum_{i=1}^{N} \left[ \frac{e(i)^2}{r(i)} + \ln|r/i| \right] + \text{cst}$$

To sum up, the complete process comprises, when we are to determine the optimum hyperparameters:

for each of the discrete values of $\mu$ chosen for the calculation of $J_2$, the estimation of a vector $\hat{a}(N/N)$ with the algorithm (10(11), with $\sigma^2 = 1$, the choice of the parameter $\hat{a}$ and of the hyperparameters $\sigma^2$ and $\mu$ corresponding to the highest likelihood; and calculation of the corresponding spectral power density $g(f)$ using the conventional relation:

$$g(f) = \sigma^2 / \left[ \left| 1 - \sum_{k=1}^{p} a_k \exp(-2i f k) \right|^2 \right] \quad (17)$$

for $$-\tfrac{1}{2} \leq f \leq +\tfrac{1}{2}$$

APPLICATION OF THE MODELLING ACCORDING TO THE INVENTION TO DOPPLER BLOOD VELOCIMETRY SIGNALS

Figure 1:
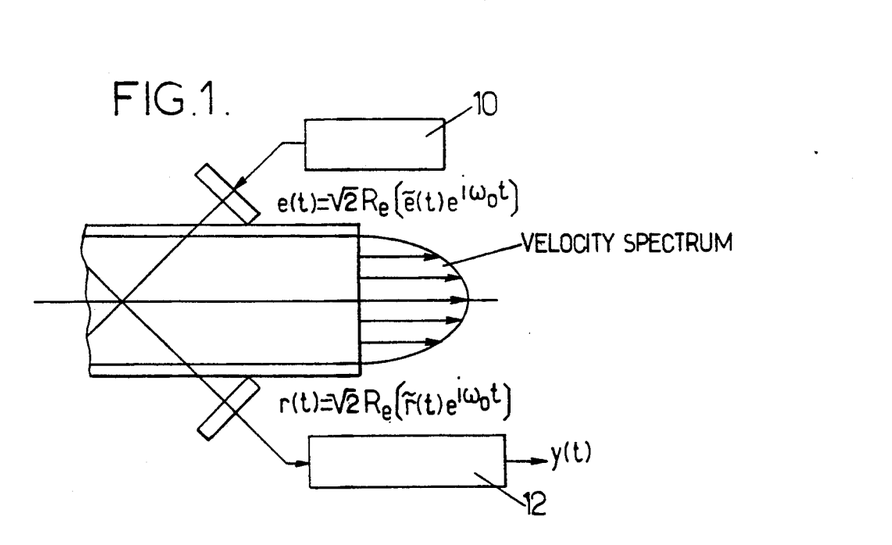
FIG. 1 is a general diagram showing the parameters used in Doppler velocimetry of the blood flow in the particular case of a continuous Doppler technique.

The choice of the duration of the self regressive model windows or blocks, of the number of samples to be taken per block, of the order of the model and of the regularizing criterion involves knowing the principal characters of the Doppler signals. These signals are obtained by a circuit of the kind shown schematically in FIG. 1. The speed field studied is illuminated by a monochromatic or pulsed acoustic wave coming from a transmitter 10 and the wave is measured which is reflected by the material targets (red blood corpuscles) moving under the action of this speed field, collected by a receiver 12 comprising a demodulator.

Figure 2:
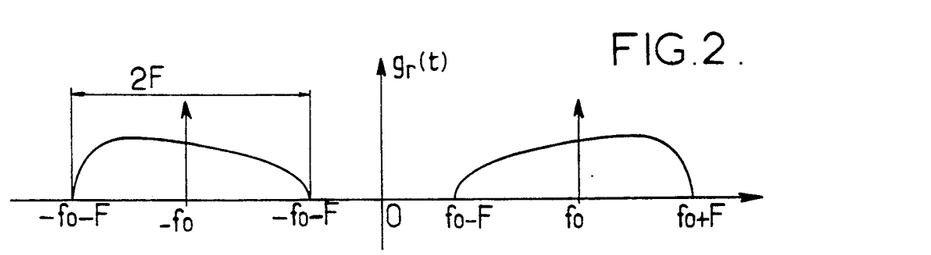
FIG. 2 is a diagram showing the envelope of a representative Doppler spectrum.

If the speed field were steady and uniform, the signal received r(t) could be derived from the transmitted signal a(t) by a simple frequency translation. This is not the case, because of the contribution of a large number of elementary targets having a dispersion with respect to the ideal mean target; the signal received has a continuous spectrum, of a narrow band width with respect to the frequency of the carrier (a few kHzas compared with a few MHz). In the frequent case of a pulsed transmission Doppler signal, the form of the transmitted wave also comes into play. In both cases a narrow band spectrum is obtained of the kind shown in FIG. 2, which is limited to two symmetrical bands of width 2F centred at $-f_0$ and $f_0$ respectively, F being very much less than the frequency $f_0$ of the carrier.

To simplify the processing of the signals, existing apparatis use demodulation, generally synchronous, which leads to breaking up the signal received r(t) into two components, respectively in phase p(t) and in quadrature q(t). These low frequency (of a few kHz) signals require a reduced sampling rate for their useful spectrum is reduced by a factor of about 1000 with respect to the carrier. The circuit may be the one shown schematically in FIG. 3.

Figure 3:
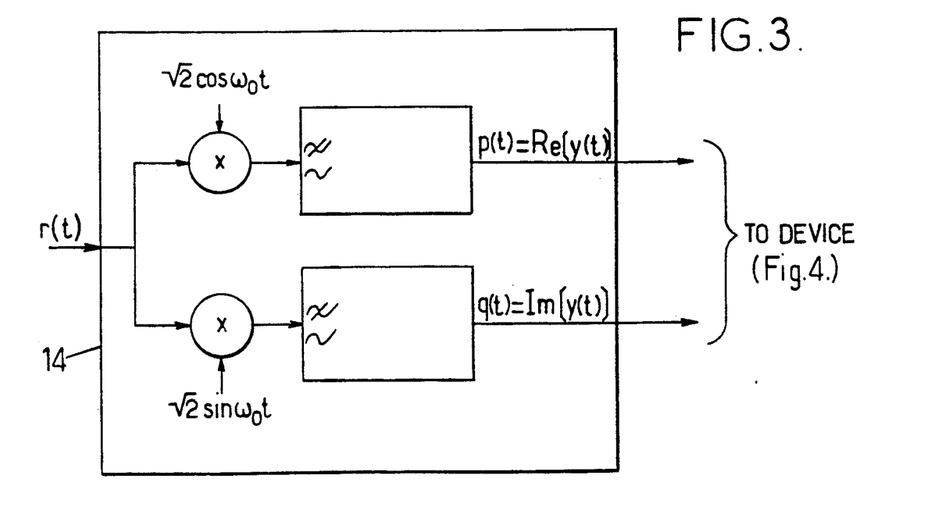
FIG. 3 is a general diagram showing demodulation of the Doppler signal.

In a complex representation we may write:

$$r(t) = \sqrt{2} \, Re\{e(t)\exp(i\omega_0 t)\}$$

where $\omega_0$ is the angular frequency the carrier and where e(t) designates the complex modulation envelope of the transmitted signal, and $$r(t) = \sqrt{2} \, p(t)\cos(\omega_0 t) + \sqrt{2} \, q(t)\sin(\omega_0 t)$$

where p(t) and q(t) are low frequency signals generated by the demodulator 14 of FIG. 3, forming respectively the real part and the imaginary part of the complex value "Doppler signal" y(t).

Calculation shows that the spectrum of the signal received r(t) can be obtained by Fourier transformation of the covariance of the Doppler signal y(t). Moreover, p(t) and q(t) are generally correlated, which prohibits assuming—nevertheless admitted in usual processing of the Doppler signal—that the mutual covariance $R_{PQ}(\tau)$ of p and q or their interspectral power density $G_{PQ}(f)$ is zero. Now, this assumption is necessary if p(t) and q(t) are processed separately.

The invention therefore processes p(t) and q(t) simultaneously, which is possible because the above described spectral analysis method has been in fact designed to be applied to complex value signals.

CHOICE OF THE REGULATION PARAMETERS IN THE APPLICATION TO DOPPLER VELOCIMETRY

Three regulation parameters must be chosen, i.e. a priori (which will be the general case since the nature of the Doppler signal is known), or following an optimization procedure.

It is a question of:

N, duration of an analysis window or length of a data block, p, order of the AR model adopted for describing the Doppler signal, $\mu$, regularization coefficient or hyperparameter.

The initialization method must also be chosen. It is defined by:

the choice of the initial parameters $a_0$ at the beginning of each block: $a_0$ may be either zero or else the result of processing of the preceding block;

the choice between the so-called "covariance" version and that called "pre-windowed".

The choice of the three parameters N, p, and $\mu$ results from a compromise. To increase N and p improves the quality of the model, but a limitation is caused by the unsteadiness of the signal which leads to reducing N and by the calculation load which leads to reducing p.

Good results are obtained with a sampling frequency of some tens of kHz and with observation windows of a maximum length of N=64 points, i.e. a maximum duration of 1 to 2 ms (instead of 5 to 10 ms in present day commercial apparatus). Since there is no need for a spectral analysis of the Doppler signal at such short time intervals, the sampled data may be organized into blocks of N=64 points at most and only working on one block out of ten. Thus, a spectral power density can be obtained every 10 to 20 ms at most, i.e. at the rate of about fifty per cardiac period.

The initialization may be achieved by pre-windowing or by covariance, as mentioned above. Pre-windowing, as used at the present time, reduces the number of multiplications to be made but adversely affects the likelihood of the model, especially if p is close to N. The covariance method reduces the maximum order of the model to p=N/2 if the recurrences are begun at time p+1 (in the case of isolated windows) and it is a little more complex.

The choice of the hyperparameter $\mu$ is essential for it governs the degree of smoothness of the solution and must maximize the likelihood of the model of the signal with respect to the data: the values of the AR parameters do not in fact depend on the variances $\sigma^2$ and $\tau^2$ but solely on their ratio $\mu$. Experience shows that the curve or variation of the likelihood as a function of $\mu$ varies very little close to the maximum and that the results of the analysis are little affected by variations of an order of size of this parameter. Experience also shows that, for a given Doppler signal, the variations of the optimum value of $\mu$ from one data block to another are also of an order of size. The complexity of the method may therefore be reduced by substituting, in the step for maximizing the likelihood of the model which must be carried out on each block of data, a previous step for classifying the signals as a function of the constant values to be attributed to For this to be possible, it is indispensable to standardize $\mu$ with respect to the power of the Doppler signal. In fact, the coefficient intervenes in the minimized criterion:

$$J_2(a) = J_1(a + \mu |a - a_0|^2 \tag{7}$$

where $J_1(a)$ has the dimension of the energy of the signal and the AR parameters are without dimension. The coefficient $\mu$ has then a dimension and varies as the square of the scale in which the Doppler signal is measured.

To make $\mu$ independent of the power of the signal, it is then necessary to choose:

$$\mu = \mu_0 \sigma^2 (N/p)$$

where $\mu_0$ is the new regulation parameter, this time without dimension, and $\sigma^2$ is the variance of the signal which may be furnished by the acquisition module of the device used (24). Such standardization makes it possible to work with a constant $\mu_0$ throughout a cardiac cycle, independently of the power fluctuations of the Doppler signal.

The invention is susceptible of numerous embodiments. In particular, the sensitivity of the process can be reduced to the limited accuracy of the calculations by propagating the square roots of the covariance matrices rather than the matrices themselves: such a modification is simple to carry out, as mentioned above.

CONSTRUCTION OF THE DEVICE

Figures 4, 5:
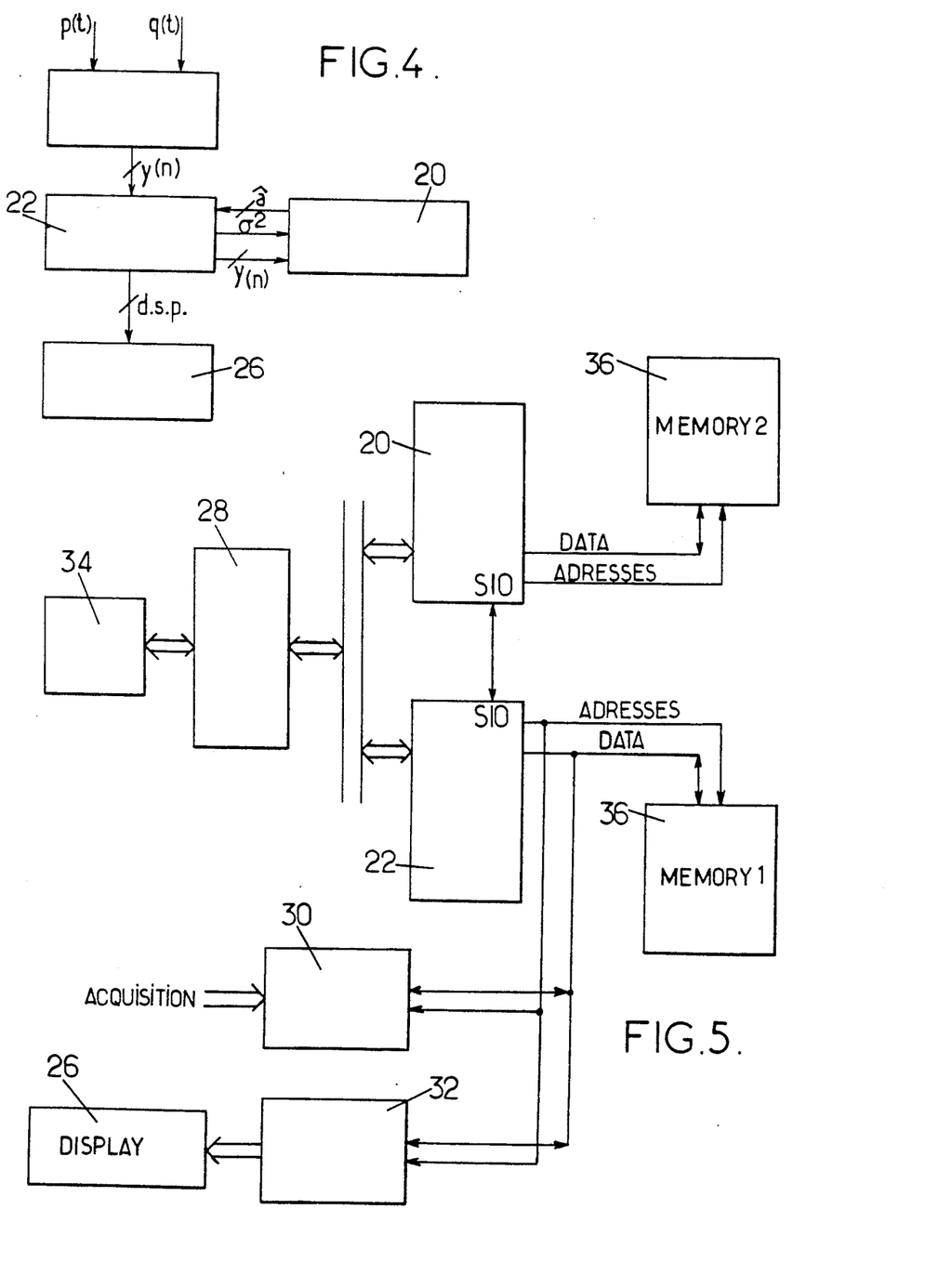
FIGS. 4 and 5 are block diagrams showing a possible implementation of the process of the invention.

The device used for implementing the process may have the general construction shown in FIG. 4, which seeks a compromise between the quality of the results and the volume of calculations, is adaptable to existing apparatus and uses the intrinsic possibilities of digital signal processors at present available.

The device comprises two processors coupled for calculating the Doppler spectrum. The first one, 20, calculates the parameters of a model of the Doppler signal received using the algorithm B-CAR. The second one, 22, delivers the spectrum from this model. This second processor 22 controls an acquisition card 24 which acquires the two Doppler channels simultaneously, at a sampling frequency which is for example of 40 kHz for studying the blood flow, chosen so as to optimize the compromise between the duration of the sections analyzed and the frequency accuracy of the spectral analysis. To avoid possible dissymmetry in the acquisition of the Doppler signals, a single converter is used. The card may be adapted for detecting possible saturation of the Doppler signals.

The processor 20 is programmed for scaling the hyperparameter $\mu$ of the method from the estimate of the instantaneous power of the Doppler signal delivered by processor 22, and calculating the AR parameters of the Doppler signal on each data block transmitted by the same module.

The processor 22 calculates the spectrum of the signal on a block, from the AR parameters delivered by processor 20 under the control of the display module 26 which fixes the number of points on the axis of the frequencies and the number of grey levels; it may be adapted for calculating a possible DC component in the acquisition chain. It must in addition evaluate the instantaneous power of the signal, used by processor 20 for optimizing the results delivered.

The architecture of the apparatus may be as shown in FIG. 5. Processor 22 executes the algorithm for calculating the spectral power density and controls the data input and output interfaces 28-30-32. Processor 20 executes the algorithm B-CAR.

A host mini computer forms a master machine which loads the programme into the processors and controls the execution of the programmes. A ROM implantation of the programme would avoid the need for a host mini computer. The acquisition 30 and display 32 interfaces transfer the data, on the one hand between the acquisition device and processor 22 and between the display device 26 and this same processor 22. Each processor has its own working memory 36.

It is necessary to carry out the calculations in a 32 bit format with floating point. Circuits available commercially respond to such needs. It is a question on the one hand of signal processors formed of a 32 bit computation unit with floating point, a control unit, memories and interface devices integrated in a single circuit (for example DSP32 of ATT and $\mu$/PD77230 of NEC), on the other hand, 32 bit arithmetic units. The process has in particular been put into practice using DSP32 processors whose internal buses are accessible from outside the case (which makes it possible to increase the memory size by 4 kbytes to 56 kbytes), and which have a parallel interface for DMA memory access whatever the activity of the processor and a high flow rate series interface (8 Mbits/second).

We claim:

1. Process for the real time spectral analysis of unsteady signals with complex values, representing a physical phenomenon, in which the phenomenon represented by the signal is modelled by a self-regressive process, characterized in that:

successive sections of the sampled signal are modelled by a high order self-regressive process, close to or equal to the maximum authorized by the duration of the sections and the sampling frequency, by estimating the parameters characterizing the model by rapid Kalman filtering using an algorithm which is simplified to the extent authorized by the local steady state of the model in the section and in that the spectral power density g(f) is determined from the estimated parameters; and in that:

the parameters a of the self-regressive model are regularized:

$$z(n) = \sum_{i=1}^{p} a_i y(n - i) = a^t y_p(n)$$

-continued with $$\begin{cases} a^t = a_p, a_{p-1}, \ldots, a_1] \\ y_p(n)^t = y(n-p), \ldots, y(n-1)] \end{cases}$$

where a is the vector of the coefficients of the model whose order is p, where b(n) represents the process generating the signal, where z(n) designates the samples of the function representing the phenomenon and where y(n) designates the observed samples, by using a constraint which consists in minimizing a criterion of the form:

$$J_2(a) = J_1(a) + \Omega(a)$$

where $J_1(a)$ is the sum of the least squares $$[y(n) - z(n)]^2,$$

and where $\Omega(a)$ is a regularizing function taking into account the a priori knowledge of the nature of the phenomenon.

2. Process according to claim 1, characterized in that $\Omega(a)$ is of the form:

$$\Omega(a) = \mu |a - a_0|^2$$

where $a_0$ is a predetermined value, chosen a priori zero or formed by the result obtained for the preceding section.

3. Process according to claim 2, characterized in that $\mu$ is taken equal to $\mu \sigma^2$ where $\mu$ is a predetermined value and $\sigma^2$ the estimated power of the signal.

4. Process according to claim 2, characterized in that the spectral power density is calculated by the relation:

$$g(f) = \sigma^2 / \left[ \left| 1 - \sum_{k=1}^{p} a \exp(-2i\pi f k) \right|^2 \right].$$

5. Process according to claim 2, characterized in that the in phase and in quadrature components of a demodulated narrow band signal are processed simultaneously.

6. Process according to claim 2, characterized in that, with the signals being demodulated Doppler signals representative of the blood flow having a frequency spectrum of a few kHz, sections of about 64 samples are used taken at a frequency of about 40 kHz and the in phase and in quadrature components of the demodulated signal are processed simultaneously.

* * * * *